US00PP32927P2

(12) United States Plant Patent
Olesen

(10) Patent No.: US PP32,927 P2
(45) Date of Patent: Mar. 30, 2021

(54) COMPACT FLORIBUNDA ROSE PLANT NAMED 'POULPAL082'

(50) Latin Name: *Rosa hybrida*
Varietal Denomination: Poulpal082

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 16/873,981

(22) Filed: Sep. 3, 2020

(51) Int. Cl.
*A01H 6/74* (2018.01)
*A01H 5/02* (2018.01)

(52) U.S. Cl.
USPC ..... Plt./144

(58) Field of Classification Search
USPC ..... Plt./144
See application file for complete search history.

(56) References Cited

PUBLICATIONS

PLUTO Plant Variety Database Nov. 4, 2020.*

* cited by examiner

*Primary Examiner* — Annette H Para

(57) ABSTRACT

A new garden rose plant of the Compact Floribunda class which has abundant, near white flowers and attractive foliage. This new and distinct variety has shown to be uniform and stable in the resulting generations from asexual propagation.

2 Drawing Sheets

Botanical designation: *Rosa hybrida.*
Variety denomination: 'Poulpal082'.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2010 and the resulting seeds were planted in a controlled environment in Fredensborg, Denmark. The new variety, named 'Poulpal082', originated as a single seedling from the stated cross.

The new variety may be distinguished from its male pollen parent and female seed parent primarily by the following characteristics. The male pollen parent plant has near white flowers with a diameter of 50 to 60 mm while the new variety has near white flowers with a diameter of 75 mm. The female seed parent plant has deep pink flowers while the new variety has near white flowers.

The objective of the hybridization of this rose variety was to create a new and distinct variety with unique qualities, such as:

1. Uniform and abundant near white flowers;
2. Vigorous, but compact growth when propagated on its own roots;
3. Exceptional disease resistance.

This combination of qualities is not present in previously available commercial cultivars of this type, known to the inventor, and distinguish 'Poulpal082' from all other varieties of which we are aware.

As part of the rose development program, Mogens N. Olesen germinated the seeds from the aforementioned hybridization during winter of 2010 and conducted evaluations on the resulting seedlings in a controlled environment in Fredensborg, Denmark. 'Poulpal082' was selected in the spring of 2011 by the inventor as a single plant from the progeny of the aforementioned hybridization.

Asexual reproduction of 'Poulpal082' by rooted cuttings was first done by Mogens N. Olesen in the nursery in Fredensborg, Denmark in July, 2011. This initial and other subsequent asexual propagations conducted in controlled environments have demonstrated that the characteristics of 'Poulpal082' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulpal082'.

Specifically illustrated in FIG. 1 of the drawings are open flowers viewed from the side and from above, petals and sepals detached showing reproductive flower parts.

Figure 1:
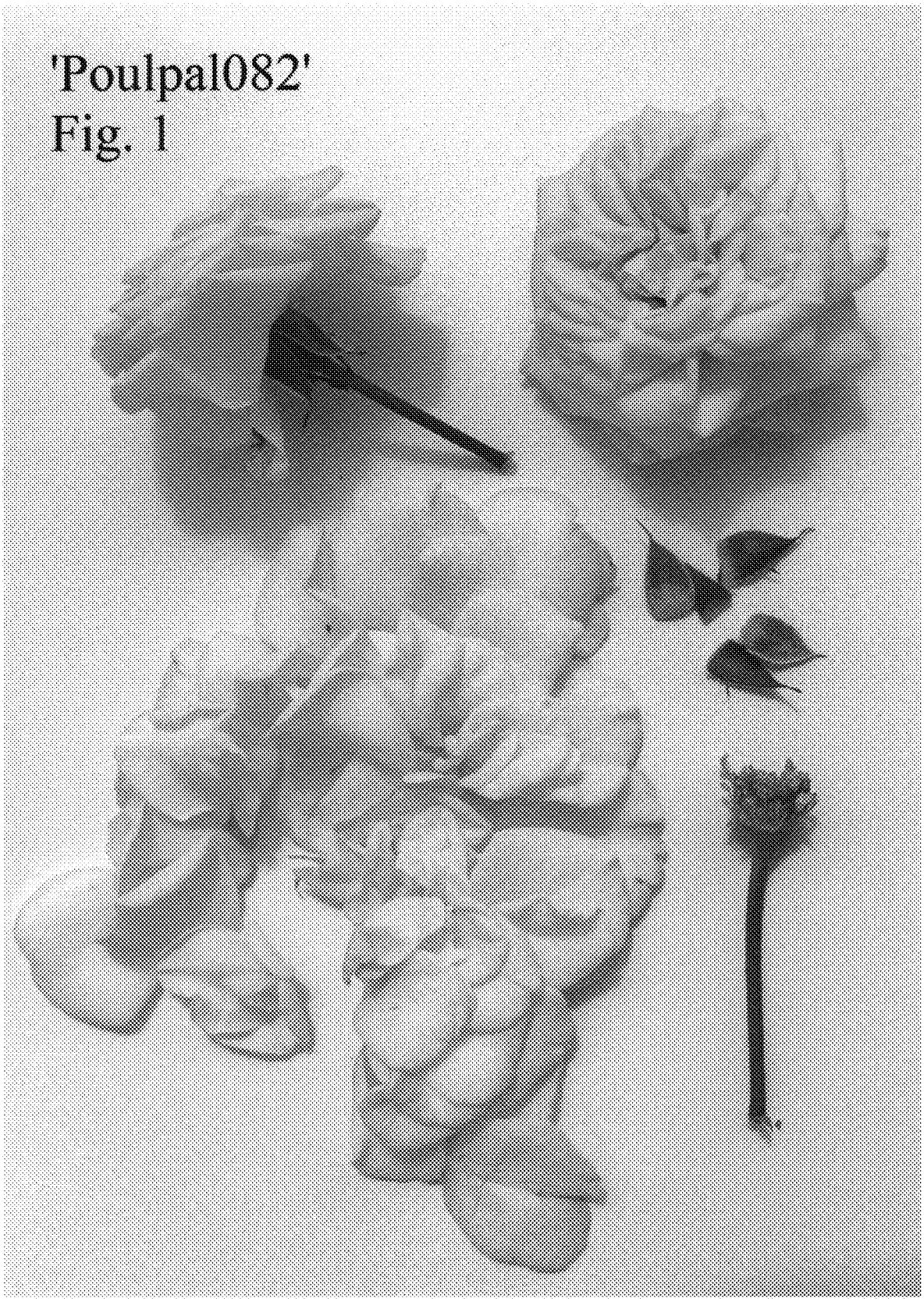
Figure 2:
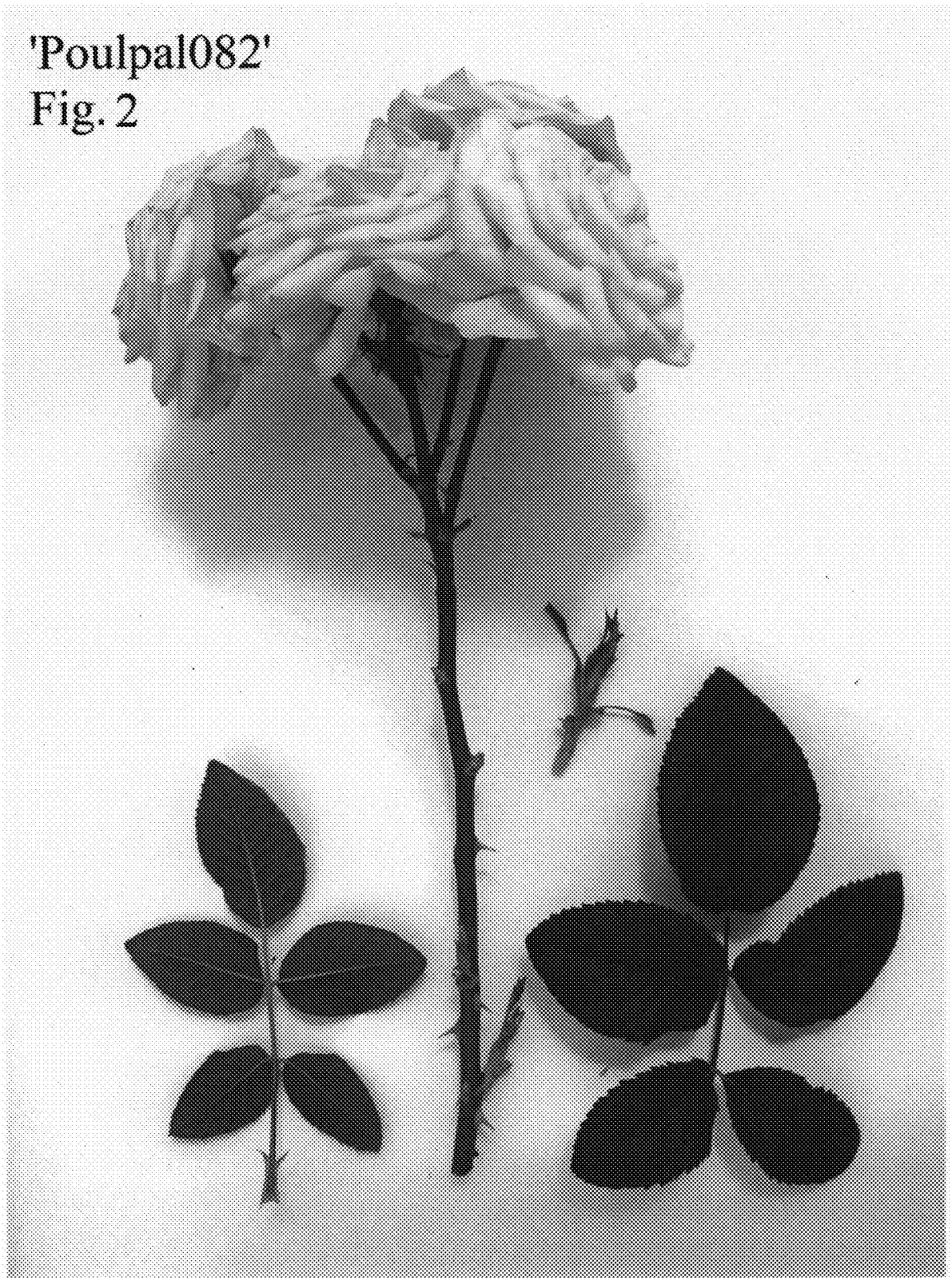

Specifically illustrated in FIG. 2 of the drawings are mature leaves, juvenile leaves, and a cluster of flowers on the branch, after they have fully matured. Plants shown are 4 months of age.

DETAILED DESCRIPTION OF THE VARIETY

The following is a description of 'Poulpal082', as observed in its growth in a controlled environment greenhouse in Odense Denmark. Observed plants are 4 months old and were grown on their own roots in 19 cm containers.

Color references are made using The Royal Horticultural Society (London, England) Colour Chart, 2001, except where common terms of color are used.

For a comparison, several physical characteristics of the rose variety 'Poulpal038', U.S. Plant Pat. No. 25,126 are compared to 'Poulpal082' in Chart 1.

CHART 1

| | 'Poulpal082' | 'Poulpal038' |
|---|---|---|
| Petal Count | 65 | 26 |
| Flower Diameter | 75 mm | 60 to 80 mm |
| General Tonality of Flower Color | Yellow Group 11D with intonations of Yellow-Orange Group 14D | White Group 155B |

FLOWER AND FLOWER BUD

Blooming habit: Continuous.

Flower bud:

*Size.*—Upon opening, 24 mm in length from base of receptacle to end of bud. Bud diameter is 16 mm.

*Bud form.*—Ovoid.

*Sepal inner surface.*—Color: Yellow-Green Group 146D. Surface: Lightly pubescent.

*Sepal outer surface.*—Color: Yellow-Green Group 144A. Texture: Smooth.

*Sepal shape.*—Apex: Cirrhose. Base: Flat at union with receptacle.

*Sepal margin.*—Margins have weak foliaceous appendages on three of the five sepals.

*Sepal size.*—20 mm long, 10 mm wide.

*Receptacle.*—Texture: Smooth. Size: 8 mm in height, 9 mm wide. Color: Yellow-Green Group 144A. Shape: Funnel.

*Pedicel.*—Surface: Smooth and with many fragrant stipitate glands. Length: 43 mm. Diameter: 3 mm on average. Color: Yellow-Green Group 144A. Strength: Strong.

*Peduncle.*—Length: 5 to 10 mm. Diameter: About 4 mm. Color: Yellow-Green Group 144A. Texture: Smooth.

Flower bud development: Flower buds are borne in clusters of about 5 flower buds per stem.

Flower bloom:

*Fragrance.*—Moderate floral scent.

*Duration.*—The blooms have a duration on the plant of approximately 10 days. Petals fall cleanly away from plant after flowers have fully matured.

*Size.*—Flower diameter is 75 mm when open. Flower depth is 30 mm.

*Flower shape.*—Rosette very double flower with many slightly overlapping petals of different sizes.

*Shape of flower, side view.*—The upper portion is convex. The lower portion is deep concave.

Petalage: Under normal conditions, flowers have about 65 petals.

General tonality of flower: Open flowers are Yellow Group 11D with intonations of Yellow-Orange Group 14D.

*Petal color.*—Upon opening, outer petals. Upper surface: White Group 155C. Lower surface: Yellow Group 4D. Upon opening, inner petals: Upper surface: Marginal zone White Group 155B. Middle zone Yellow Group 8B. The basal zone is Yellow Group 8A. Lower surface: Yellow Group 4D at the marginal zone. At the middle and basal zone Yellow Group 8C. Basal petal spots, upon opening: Upper surface: Yellow Group 5C. Lower surface: Yellow Group 5C. After opening, outer and inner petals. Upper surface: Green White Group 157D, with intonations of Yellow-Green Group 145D. at the margins. Lower surface: Marginal zone Yellow-Green Group 145C. At the middle and basal zone Green White Group 157C. Basal petal spots, after opening: No distinctive coloration at the petal base observed.

Petals:

*Petal reflex.*—Strong, bilateral.

*Margin.*—Entire and uniform. Moderate undulations.

*Shape.*—Broad and elliptic. Apex shape: Rounded. Base shape: Obtuse.

*Size.*—About 35 mm (l)×36 mm (w).

*Texture.*—Smooth.

*Thickness.*—Above average.

Petaloids:

*Size.*—20 mm (l) by 14mm (w).

*Quantity.*—About 10.

*Shape.*—Elliptical with an acute base and rounded apex.

*Color.*—On the upper size White Group 155B with strong intonations of Yellow Group 8A and 8B. On the lower surface Yellow Group 4D with basal intonations of Yellow Group 8C.

Reproductive flower parts:

*Pollen.*—None observed.

*Anthers.*—Size: 2 mm in length. Color: Greyed-Yellow Group 160D. Quantity: 30 on average.

*Filaments.*—Color: Yellow Group 13B. Length: 6 mm.

*Pistils.*—Length: 6 mm. Quantity: 45 on average.

*Stigmas.*—Color: Greyed-Yellow Group 160B

*Styles.*—Color: Green White 157A with intonations of Red Group 39A.

*Location of stigmas.*—Inferior in location relative to the length of the filaments and the height of the anthers.

*Hips.*—None Observed.

PLANT

Plant growth: Upright and compact. Plants are about 50 cm in height, and 45 cm wide.

Stems:

*Color of juvenile growth.*—Yellow-Green Group 144B.

*Color of mature growth.*—Yellow-Green Group 144A.

*Length.*—Canes are about 30 cm from the base of the plant to the flowering portion.

*Diameter.*—About 5 mm on mature stems.

*Internodes.*—About 45 mm between nodes.

*Surface texture.*—Young wood: Smooth. Older wood: Smooth.

Long prickles:

*Incidence.*—5 prickles per 10 cm of stem.

*Size.*—Average length of prickles on mature stems is 7 mm.

*Shape.*—Upper portion is linear. Lower portion is concave.

*Color.*—Juvenile prickles: Greyed-Yellow Group 161B. Mature prickles: Greyed-Orange Group N167C and Greyed-Yellow Group 161B.

Plant foliage:

*Compound leaf.*—150 mm (l)×110 (w).

*Quantity.*—2 leaves per 10 cm of stem on average.

*Leaf bearing angle to the stem.*—45 degrees.

*Color of juvenile foliage*.—Upper side: Yellow-Green Group 144A with intonations of Greyed-Purple Group 183A. Lower side: Yellow-Green Group 144B and Greyed-Purple Group 183A.

*Color of mature foliage*.—Upper side: Yellow-Green Group 147A. Lower side: Yellow-Green Group 147B.

Plant leaves and leaflets:

*Stipules*.—Size: 6 mm long, mm wide. Quantity: 2 per compound leaf. Shape: Linear, slightly broad based with outward extending apices. Margins: Finely serrated. Color:

*Petiole*.—Length: 27 mm. Diameter: 2 mm. Upper surface color: Yellow-Green Group 144A. Lower surface color: Yellow-Green Group 144A.

*Rachis*.—Length: 48 mm. Upper surface color: Yellow-Green Group 144A. Lower surface color: Yellow-Green Group 144A.

*Leaflet*.—Quantity: Normally 5 leaflets. Margins: Double serrated. Size: Terminal leaflets are about 65 mm long, 42 mm wide. Shape: Generally elliptical. Base: Rounded. Apex: Acute. Texture: Smooth. Thickness: Average. Arrangement: Odd pinnate. Venation: Reticulate. Glossiness: Moderately glossy.

Disease resistance: Above average resistance to powdery mildew *Sphaerotheca pannosa* var. *rosae*, downy mildew *Peronospora sparsa*, rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant of the Compact Floribunda rose class named 'Poulpal082', substantially as illustrated and described herein, due to its abundant near white flowers, disease resistance, and extended period of bloom.

* * * * *

'Poulpal082'

'Poulpal082'